United States Patent [19]

Piret et al.

[11] 3,944,836

[45] Mar. 16, 1976

[54] AUXILIARY COLLIMATING DEVICE FOR OBTAINING IRRADIATION FIELDS OF ANY SHAPE FOR HIGH ENERGY RADIOTHERAPY APPARATUS

[75] Inventors: Pierre Piret, Liege; Hubert Fraikin, Bassenge; Armand Hubert, Liege, all of Belgium

[73] Assignee: C.G.R. -MeV, Paris, France

[22] Filed: Apr. 5, 1974

[21] Appl. No.: 458,445

[30] Foreign Application Priority Data
 Apr. 10, 1973  Belgium .............................. 798040

[52] U.S. Cl. ................................ 250/505; 250/514
[51] Int. Cl.² ........................ A61N 5/10; G21K 1/04
[58] Field of Search ............ 250/505, 514, 512, 511

[56] References Cited
 UNITED STATES PATENTS
 2,871,367  1/1959  Gournay .............................. 250/505
 3,114,043  12/1963  Thomas et al. ...................... 250/505
 3,805,081  4/1974  Barthel et al. ...................... 250/512

FOREIGN PATENTS OR APPLICATIONS
 1,529,604  5/1968  France ............................... 250/514

Primary Examiner—James W. Lawrence
Assistant Examiner—T. N. Grigsby
Attorney, Agent, or Firm—Cushman, Darby & Cushman

[57] ABSTRACT

An auxiliary collimator is added to the main collimator of a radiotherapy apparatus and comprises a master-container filled with mercury and a localising container containing a block of non absorbent material having a predetermined shape; means being provided for automatically positioning these containers with respect to the main collimator and for allowing the mercury to enter the localising container when once it has taken its working position.

4 Claims, 1 Drawing Figure

U.S. Patent    March 16, 1976    3,944,836
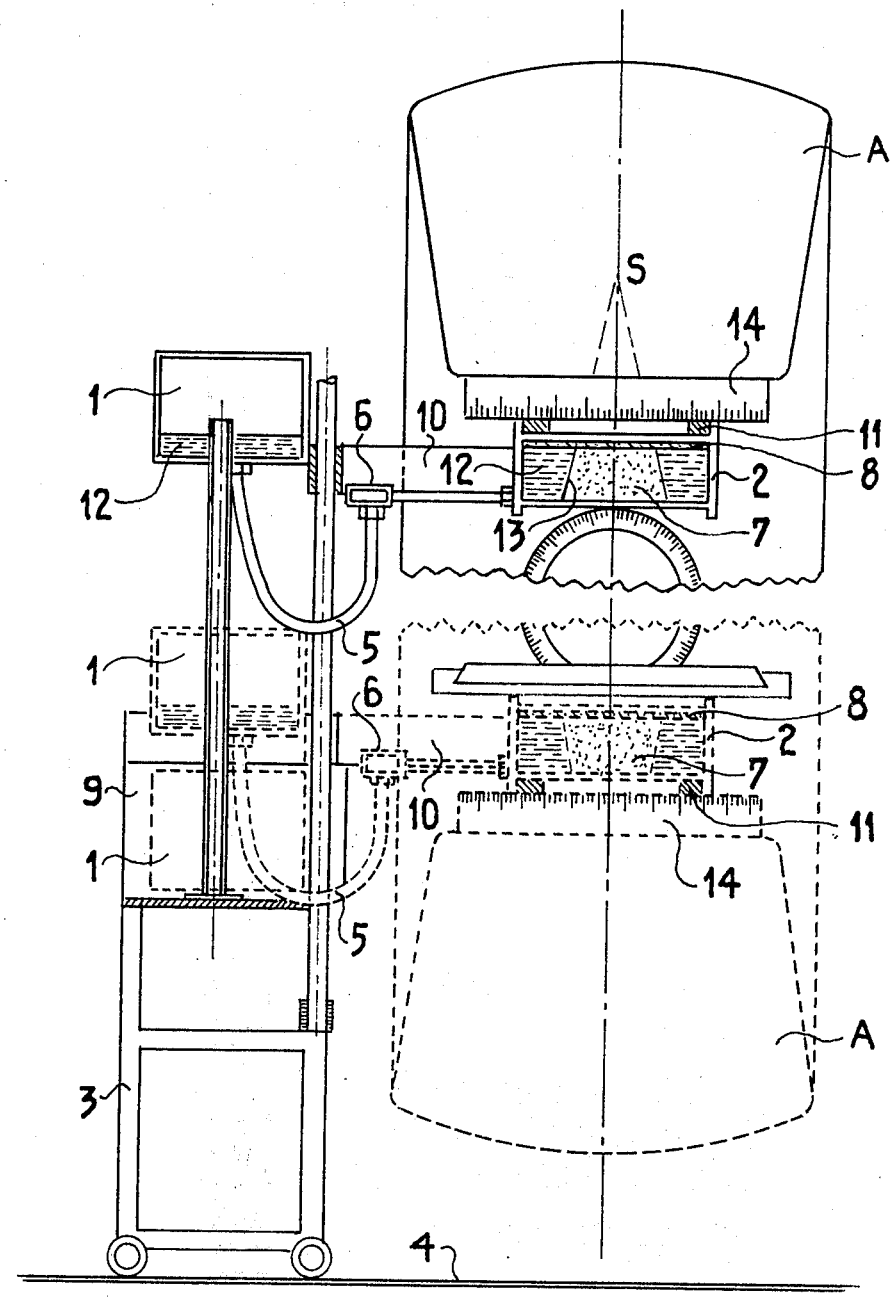

AUXILIARY COLLIMATING DEVICE FOR OBTAINING IRRADIATION FIELDS OF ANY SHAPE FOR HIGH ENERGY RADIOTHERAPY APPARATUS

The present invention relates to an auxiliary collimating device for obtaining irradiation fields of any shape for high-energy radiotherapy apparatus.

For the high-energy irradiation (accelerators, $Co^{60}$) of fields of large size and irregular shape —in particular in the case of Hodgkin's disease— the delimitation of the volume to be irradiated usually requires the use of large size, heavy equipment which is not easy to handle and only allows an unprecise localization of the region to be irradiated with respect to the beam.

The device according to the invention satisfies the following requirements in addition to the delimitation of an irradiation field of any shape and to a convergence of the lateral walls of the auxiliary collimator toward the source of radiation :

possible utilisation of the treating apparatus provided with such a device for the two vertical shooting positions of the treating apparatus;

no assemblage elements along the path of useful radiation;

minimum overall size and weight;

remote controlled positioning with no danger to the patient placed on the treating table;

maximum distance between the outlet of the auxiliary collimator and the skin of the patient so as to reduce as far as possible the secondary radiation which is produced by the presence of the device and reaches the patient.

In accordance with the invention, there is provided an auxiliary collimating device for obtaining irradiation fields of any shape for radiotherapy apparatus provided with a source of high-energy particules and a main collimator, said auxiliary collimating device comprising a first container termed a master-container and a second container, termed a localising container, said two containers being integral with a chassis movable along guide rails; said containers being interconnected by a flexible pipe; the master-container being, in a position of rest, filled with mercury; said localising container containing a block of expanded polystyrene of predetermined shape; said block having lateral walls converging toward said source of particles, said block having cross sections the dimensions of which are homothetic to dimensions of the field to be irradiated midway of the depth of the volume to be treated.

Also according to the invention, the two containers are associated with first shifting means for imparting to said containers a vertical movement at two preselected speeds, said movement allowing a suitably positioning of said containers for an irradiation shooting successively downwardly and upwardly, a high-speed travel being arranged for placing said containers in the vicinity of their working position and low-speed travel enabling said localising container to be positioned positioned with precision against said main collimator, said master-container being associated with second shifting means for placing the master-container filled with mercury in a predetermined upper position with respect to the localising container, so as to allow the mercury contained in the master-container to enter the localising container and fill the volume left free by said polystyrene block disposed in said localising container.

A better understanding of the invention will be had and further features will be apparent, from the ensuing description with reference to the accompanying drawing.

As can be seen in the figure, the auxiliary collimator comprises a first container termed a master container 1 and a second container termed a localising container 2. These containers are mounted on a chassis 3 which is movable along guide rails 4.

The two containers 1, 2 have a rectangular sided shape in the illustrated embodiment and are interconnected by a flexible pipe 5, directly or through an auxiliary container 6 the function of which will be explained hereinafter.

In the position of rest, the master container 1 is filled with mercury 12 on which water, possibly containing detergent, floats. The water serves to isolate the mercury 12 from the air of the treating premises so as to avoid the contamination of the premises by the mercury 12 owing to its high vapour tension.

At rest, the auxiliary container 6 is filled with water containing detergent and this water is sent to the localising container 2 in the working position and performs therein the same isolating function as that described hereinbefore in respect of the master container 1.

For a given field to irradiate, that is a patient the container 2 is provided with a block 7 of expanded polystyrene of predetermined shape which material is particularly radio-transparent. This block 7 has lateral walls the inclination of which is such that these walls all converge toward the source S of irradiation, the crossections of the block 7 having dimensions which are homothetic dimensions of the field to be irradiated at midway of the depth of the volume to be treated. This block 7 is adhered to a rectangular methyl polymethacrylate (T.M. plexiglass) plate 8 having a thickness of about 2 mm, its length and width being substantially identical to the length and width of the localising container 2 so as to permit a precise positioning of the block 7 in the container 2. The overall thickness of the block 7 of polystyrene and the plate 8 is slightly less than the height of the container so that the pressure exerted by the mercury 12 can maintain the upper face of the plate 8 of plexiglass against the upper wall of the container 2.

The containers 1, 2 are disposed on a movable assembly 9 provided with two arms 10 (only one arm 10 is shown in figure) for supporting the container 2, and are associated with first shifting means for imparting to them a vertical movement enabling the container 2 to be placed in the position for irradiation by shooting downwardly (position shown in full line) or in the position for irradiation shooting upwardly (position shown in dotted line.) The higher speed can only be engaged if the auxiliary localiser 2 is remote from the treating apparatus A. The high-speed travel is adjusted to place the container 2 in the vicinity of its working position, whereas the low-speed travel serves to place the localising container 2 against a main collimator 14 integral with the treating apparatus A and this can only be achieved, owing to the provision of safety devices, if the localising container 2 is correctly positioned for the considered irradiations. Other safety systems stop the travel at low speed if the container 2 is not facing a support base 11 integral with the treating apparatus A.

A further system ascertains the contact between the auxiliary container 2 and the main collimator 14 of the treating apparatus A and automatically stops the drives ensuing the movement of the treating apparatus A, and in particular the rotation of the radiotherapy head and of the main collimator 14 integral therewith, when the contact is established.

When the localising container 2 bears against the main collimator 14 of the treating apparatus A, it is united with the latter by a locking which starts up the drive of second shifting means which impart to the master container 1 the upper position with respect to the localising container 2 for filling with mercury 12 the volume left free by the polystyrene block 7 disposed in the localising container 2. When the mercury 12 reaches a required height in the container 2 (7 cm in the illustrated embodiment) it closes the contacts which stop the rising movement of the master container 1.

The localising container 2 according to the invention is brought in contact with the base of the main collimator 14 of the treating apparatus A in such manner as to present a cross section of minimum dimensions. The utilisation of mercury 12 in the localising container 2 enables the thickness of the latter to be reduced with respect to conventional localisers constructed with bricks or balls of lead.

The positioning of the localising container 2 is particularly precise and fully remote-controlled.

The device according to the invention also permits an irradiation of the regions to be treated from the front and from the rear while allowing the patient to maintain the same position of decubitus dorsal, the natural condition for increasing the comfort of the patient and the precision of the application of the treating plane. This feature offers in particular the essential advantage of avoiding any over-dose or under-dose in the region of the interval organs, which phenomenon is related to the necessarily different positions of these organs when the patient is obliged to occupy for the treatment two different positions.

The device according to the invention is particularly applicable to a linear accelerator, but it is also of utility in other machines.

What we claim is:

1. An auxiliary collimating device for obtaining irradiation fields of any shape for irradiation apparatus provided with a source of highenergy particles and a main collimator, said auxiliary collimating device comprising a first container, termed a master container, and a second container, termed a localising container, said containers being integral with a chassis movable along guide rails; said containers being interconnected by a flexible pipe; said master container being, in a position of rest, filled with mercury ; said localising container containing a block of expanded polystyrene of predetermined shape; said block having lateral walls converging toward said source of particles; the block having cross-section the dimensions of which are homothetic to the dimensions of the field to be irradiated midway of the depth of the volume to be treated.

2. An auxiliary collimating device as claimed in claim 1, wherein said master-container and said localising container are associated with first shifting means for imparting to said containers a vertical movement at two pre-selected speeds, said movements allowing a suitably positioning of said containers for an irradiation shooting successively downwardly and upwardly, the high-speed travel enabling said localising container to be placed rapidly substantially in the region of its working position and the low-speed travel enabling said localising container to be positioned with precision against said main collimator; said master container being associated with second shifting means for placing said master container filled with mercury in a predetermined upper position with respect to the localising container so as to allow the mercury contained in the master container to enter the localising container and fill the volume left free by said polystyrene block disposed in said localising container.

3. An auxiliary collimating device according to claim 1, wherein said mercury contained in said master container is covered with water and there is disposed between said master container and said localising container an auxiliary container containing water which is adapted to be supplied to the localising container so as to cover the mercury contained in the localising container.

4. An auxiliary collimating device according to claim 1, wherein said expanded polystyrene block is adhered to a methyl polymethacrylate plate whereby said block may be positioned with precision in said localising container, the thickness of the assembly formed by said plate and said block being less than the height of said container.

* * * * *